United States Patent
Bassett et al.

[11] Patent Number: 6,086,371
[45] Date of Patent: Jul. 11, 2000

[54] DENTAL IMPLANT DELIVERY SYSTEM HAVING DRIVER MOUNT WITH REMOVABLE FLANGE

[75] Inventors: Jeffrey A. Bassett, Vista; James I. Johnson, Sun City; William R. Wagner, Escondido, all of Calif.

[73] Assignee: Sulzer Orthopedics Inc., Austin, Tex.

[21] Appl. No.: 09/019,000

[22] Filed: Feb. 5, 1998

[51] Int. Cl.⁷ .................................................. A61C 8/00
[52] U.S. Cl. ........................ 433/173; 206/339; 206/63.5
[58] Field of Search .................................. 433/172, 173, 433/174, 175, 176, 201.1; 206/63.5, 338, 339, 363, 438

[56] References Cited

U.S. PATENT DOCUMENTS

| | | |
|---|---|---|
| Re. 8,112 | 3/1878 | Frazier . |
| D. 351,904 | 10/1994 | Maze ...................................... D24/121 |
| 394,376 | 12/1888 | Kelton . |
| 2,112,007 | 3/1938 | Adams ........................................... 32/2 |
| 3,067,740 | 12/1962 | Haboush ................................... 128/92 |
| 3,488,779 | 1/1970 | Christensen ..................................... 3/1 |
| 3,846,846 | 11/1974 | Fischer ............................................ 3/1 |
| 3,990,438 | 11/1976 | Pritchard .................................. 128/92 |
| 4,027,392 | 6/1977 | Sawyer et al. ............................... 32/10 |
| 4,145,764 | 3/1979 | Suzuki et al. ................................ 3/1.9 |
| 4,177,562 | 12/1979 | Miller et al. . |
| 4,180,192 | 12/1979 | Breslau .................................... 224/235 |
| 4,234,309 | 11/1980 | Sellers ..................................... 433/225 |
| 4,259,072 | 3/1981 | Hirabayashi et al. ................... 433/173 |
| 4,414,966 | 11/1983 | Stednitz ................................. 128/92 B |
| 4,424,037 | 1/1984 | Ogino et al. ............................ 433/173 |
| 4,444,310 | 4/1984 | Odell ....................................... 206/366 |
| 4,463,753 | 8/1984 | Gustilo ................................. 128/92 B |
| 4,468,200 | 8/1984 | Munch .................................... 433/174 |
| 4,480,997 | 11/1984 | Deutsch et al. ......................... 433/221 |
| 4,484,570 | 11/1984 | Sutter et al. .......................... 128/92 D |
| 4,495,664 | 1/1985 | Blanquaret ................................ 3/1.913 |
| 4,511,335 | 4/1985 | Tatum, Jr. ............................... 433/173 |
| 4,535,487 | 8/1985 | Esper et al. ............................... 623/22 |
| 4,537,185 | 8/1985 | Stednitz ................................. 128/92 B |
| 4,553,942 | 11/1985 | Sutter ...................................... 433/225 |
| 4,615,462 | 10/1986 | Sacherer et al. ......................... 220/339 |
| 4,668,191 | 5/1987 | Plischka ................................. 433/174 |
| 4,671,410 | 6/1987 | Hansson et al. ......................... 206/438 |
| 4,712,681 | 12/1987 | Branemark et al. ..................... 206/438 |
| 4,713,003 | 12/1987 | Symington et al. ..................... 433/173 |
| 4,713,004 | 12/1987 | Linkow et al. .......................... 433/174 |
| 4,717,018 | 1/1988 | Sacherer et al. ......................... 206/305 |
| 4,722,688 | 2/1988 | Lonca ..................................... 433/173 |
| 4,722,733 | 2/1988 | Howson ................................... 604/411 |
| 4,738,623 | 4/1988 | Driskell .................................. 433/173 |
| 4,758,161 | 7/1988 | Niznick .................................. 433/173 |
| 4,763,788 | 8/1988 | Jorneus et al. .......................... 206/438 |
| 4,790,753 | 12/1988 | Fradera ................................... 433/174 |
| 4,793,808 | 12/1988 | Kirsch .................................... 433/173 |
| 4,826,434 | 5/1989 | Krueger .................................. 433/174 |
| 4,851,008 | 7/1989 | Johnson .................................... 623/16 |
| 4,854,872 | 8/1989 | Detsch .................................... 433/173 |
| 4,856,648 | 8/1989 | Krueger .................................. 206/63.5 |
| 4,856,994 | 8/1989 | Lazzara et al. .......................... 433/173 |
| 4,863,383 | 9/1989 | Grafelmann ............................ 433/174 |
| 4,878,915 | 11/1989 | Brantigan ................................. 623/17 |
| 4,915,628 | 4/1990 | Linkow et al. .......................... 433/173 |
| 4,915,629 | 4/1990 | Sellers .................................... 433/173 |

(List continued on next page.)

FOREIGN PATENT DOCUMENTS

| | | |
|---|---|---|
| 0312698 | 4/1998 | European Pat. Off. . |
| 30 43 336 | 6/1981 | Germany . |
| 1662545 | 7/1991 | U.S.S.R. . |
| 1727808 | 4/1992 | U.S.S.R. . |
| 1291470 | of 0000 | United Kingdom . |

OTHER PUBLICATIONS

U.S. application No. 08/689,696 for Dental Implant Delivery System, filed on Aug. 16, 1996, Inventor Michael John Biggs.

*Primary Examiner*—Nicholas D. Lucchesi
*Attorney, Agent, or Firm*—Philip S. Lyren; Kenneth S. Barrow

[57] ABSTRACT

A dental implant delivery system comprising a vial housing an implant and driver mount with a removable flange.

17 Claims, 4 Drawing Sheets

U.S. PATENT DOCUMENTS

| | | | |
|---|---|---|---|
| 4,927,363 | 5/1990 | Schneider | 433/173 |
| 4,932,868 | 6/1990 | Linkow et al. | 433/174 |
| 4,934,935 | 6/1990 | Edwards | 433/174 |
| 4,942,991 | 7/1990 | Lyons | 224/196 |
| 4,955,811 | 9/1990 | Lazzara et al | 433/173 |
| 4,960,381 | 10/1990 | Niznick | 433/174 |
| 4,976,617 | 12/1990 | Carchidi | 433/141 |
| 4,978,007 | 12/1990 | Jacobs et al. | 206/469 |
| 4,978,350 | 12/1990 | Wagenknecht | 606/72 |
| 4,988,299 | 1/1991 | Branemark | 433/174 |
| 5,015,186 | 5/1991 | Detsch | 433/173 |
| 5,018,970 | 5/1991 | Stordahl | 433/75 |
| 5,026,280 | 6/1991 | Durr et al. | 433/175 |
| 5,026,285 | 6/1991 | Durr et al. | 433/173 |
| 5,030,095 | 7/1991 | Niznick | 433/173 |
| 5,030,096 | 7/1991 | Hurson et al. | 433/173 |
| 5,035,619 | 7/1991 | Daftary | 433/173 |
| 5,049,073 | 9/1991 | Lauks | 433/173 |
| 5,061,181 | 10/1991 | Niznick | 433/174 |
| 5,062,800 | 11/1991 | Niznick | 433/229 |
| 5,064,425 | 11/1991 | Branemark et al. | 606/72 |
| 5,069,336 | 12/1991 | Mauthe | 206/219 |
| 5,073,111 | 12/1991 | Daftary | 433/173 |
| 5,076,788 | 12/1991 | Niznick | 433/173 |
| 5,078,607 | 1/1992 | Niznick | 433/174 |
| 5,100,323 | 3/1992 | Friedman et al. | 433/173 |
| 5,106,300 | 4/1992 | Voitik | 433/173 |
| 5,117,976 | 6/1992 | Whitt et al. | 206/333 |
| 5,125,840 | 6/1992 | Durr et al. | 433/173 |
| 5,135,394 | 8/1992 | Hakamatsuka et al. | 433/173 |
| 5,145,372 | 9/1992 | Daftary et al. | 433/173 |
| 5,167,664 | 12/1992 | Hodorek | 606/73 |
| 5,180,303 | 1/1993 | Hornburg et al. | 433/173 |
| 5,188,800 | 2/1993 | Green, Jr. et al. | 422/23 |
| 5,197,881 | 3/1993 | Chalifoux | 433/173 |
| 5,205,745 | 4/1993 | Kamiya et al. | 433/173 |
| 5,209,659 | 5/1993 | Friedman et al. | 433/173 |
| 5,254,005 | 10/1993 | Zuest | 433/173 |
| 5,269,685 | 12/1993 | Jorneus et al. | 433/174 |
| 5,270,011 | 12/1993 | Altherr | 422/102 |
| 5,281,140 | 1/1994 | Niznick | 433/172 |
| 5,282,746 | 2/1994 | Sellers et al. | 433/172 |
| 5,297,963 | 3/1994 | Daftary | 433/172 |
| 5,312,254 | 5/1994 | Rosenlicht | 433/173 |
| 5,312,256 | 5/1994 | Scortecci | 433/174 |
| 5,324,199 | 6/1994 | Branemark | 433/174 |
| 5,362,235 | 11/1994 | Daftary | 433/172 |
| 5,364,268 | 11/1994 | Lazzara et al. | 433/173 |
| 5,366,374 | 11/1994 | Vlassis | 433/165 |
| 5,368,160 | 11/1994 | Leuschen | 206/339 |
| 5,415,545 | 5/1995 | Shaw | 433/173 |
| 5,431,567 | 7/1995 | Daftary | 433/172 |
| 5,435,723 | 7/1995 | O'Brien | 433/174 |
| 5,449,291 | 9/1995 | Lueschen et al. | 433/173 |
| 5,484,285 | 1/1996 | Morgan et al. | 433/173 |
| 5,538,428 | 7/1996 | Staubli | 433/173 |
| 5,582,299 | 12/1996 | Lazzara et al. | 206/63.5 |
| 5,591,029 | 1/1997 | Zuest | 433/173 |
| 5,622,500 | 4/1997 | Niznick | 433/173 |
| 5,667,094 | 9/1997 | Rapchak et al. | 220/339 |
| 5,695,336 | 12/1997 | Lazzara et al. | 433/173 |
| 5,702,346 | 12/1997 | Lazzara et al. | 433/173 |
| 5,709,547 | 1/1998 | Lazzara et al. | 433/174 |
| 5,711,468 | 1/1998 | Shoemaker | 224/251 |

DENTAL IMPLANT DELIVERY SYSTEM HAVING DRIVER MOUNT WITH REMOVABLE FLANGE

BACKGROUND OF THE INVENTION

Dental implants are typically packaged and shipped in a package or implant delivery system. The delivery system, in conjunction with outside packaging, maintains the implant in a sterile environment and is opened just before the implant is needed during the surgical procedure.

FIG. 1 illustrates an example of one such prior delivery system shown generally at 10. Delivery system 10 includes a vial 12 housing a threaded implant 14 and a driver mount 16.

The vial typically has an elongated cylindrical configuration and is used to transport the implant and driver mount. A lid, not shown, fits on top of the vial to seal and retain the implant and driver mount.

Implant 14 is shown having an external threaded section 18 and a top coronal section 20. The coronal section includes a hexagonal projection 22 for mating with different dental components.

The driver mount includes a bottom portion having a hexagonal recess 24 that engages with the projections 22 on the implant. The driver mount also includes a bottom portion and a top portion having a flange 26. This flange is integrally formed with the top portion and extends outwardly to have a larger diameter than the bottom portion.

The driver mount and implant together fit within a cylindrical cavity formed within the vial. A screw 28 secures the driver mount to the implant. As shown in FIG. 1, the vial includes an internal shoulder 30 with an opening 32. The implant passes through this opening until the flange of the driver mount abuts against the shoulder. The flange and shoulder thus hold the implant and the driver mount in the vial and keep the implant from touching the sides or bottom of the vial.

In order to install implant 14 into the patient's jawbone, an implant site is prepared using conventional surgical procedures. Typically, an incision is made along the gingival tissue at the implant site, and a cylindrical bore is drilled into the alveolar bone. Once the site is fully prepared, a driving tool, such as a motorized dental hand-piece, is connected to the driver mount using an adapter. The implant and driver mount are removed from the vial. The end of the implant is fit within the bore, and the driver mount drives the implant into position. The screw and driver mount are then removed from the implant. The gingival tissue is then sutured and the implant remains within the bone for several months as osseointegration and healing occur. During a second surgical procedure, the implant is re-exposed and a dental prosthesis is affixed to the implant.

One important disadvantage associated with prior art delivery systems is that the driver mount will not fit within some tight interdental spaces. During a single tooth restoration, for example, the implant often must be driven between two adjacent teeth. The distance between these teeth may be narrow, and the flange on the driver mount may be too wide to fit. The driver mount thus cannot be used to fully seat the implant. In such a situation, a second and narrower driver must be substituted for the driver mount having a flange.

Another disadvantage is more surgical steps are required during some implantation procedures using prior art delivery systems. Again, if the interdental space is too narrow then the flange on the driver mount may prohibit the implant from being fully and properly seated in the bone. In this case, the driver mount having an integral flange must be disengaged from the driving tool and then disengaged from the implant. Next, another narrower driver mount must be attached to the implant and then attached to the driving tool. These steps not only add time to the surgical procedure but also increase inconvenience for the surgeon. Further, the risk of contaminating the implant or dropping one of the dental components also greatly increases.

It therefore would be advantageous to employ a dental implant delivery system that could be used in instances when access to the restoration site is narrow or limited in space. Such a delivery system would be more universal and could be utilized even when the interdental space is small.

It would be advantageous to employ a dental delivery system that requires a fewer number of steps during the surgical implantation procedure. A surgical procedure requiring fewer steps ultimately would be less traumatic to the patient, more expeditiously performed, and less burdensome on the surgeon, to name a few examples. Further yet, such a delivery system would minimize the amount of handling of the system components.

The present invention solves the problems discussed with prior dental delivery systems and provides further advantages.

SUMMARY OF THE INVENTION

The present invention is directed toward a dental implant delivery system that may be used in narrow interdental spaces. The delivery system includes an implant, a driver mount, a screw connecting the driver mount to the implant, and a vial for housing the components.

The driver mount consists of a core body having a removable flange. The core body has a generally cylindrical configuration and preferably a diameter that is not substantially larger than the diameter of the implant. The flange is positioned around the core body and has a diameter larger than the core body.

During transportation and storage of the delivery system, the implant and driver mount are suspended within the vial as the flange on the driver mount abuts against a ledge in the vial. Subsequently, during the surgical implantation procedure, the implant and accompanying driver mount are positioned at the osteotomy site. The driver mount is then used to drive and seat the implant. If the interdental space is narrow and cannot accommodate the size of the flange, a separate driver mount is not required. Rather, the flange is removed from the core body, and the driver mount is used to fully seat and position the implant.

The delivery system of the present invention is particularly advantageous because it may be used in narrow interdental spaces. Further, additional surgical steps of removing one driver mount and substituting a narrower one are not required.

The invention, accordingly, comprises the apparatus and method possessing the construction, combination of elements, and arrangement of parts which are exemplified in the following detailed description. For a fuller understanding of the nature and objects of the invention, reference should be made to the following detailed description taken in connection with the accompanying drawings.

DETAILED DESCRIPTION OF THE PREFERRED EMBODIMENTS

Figure 1:
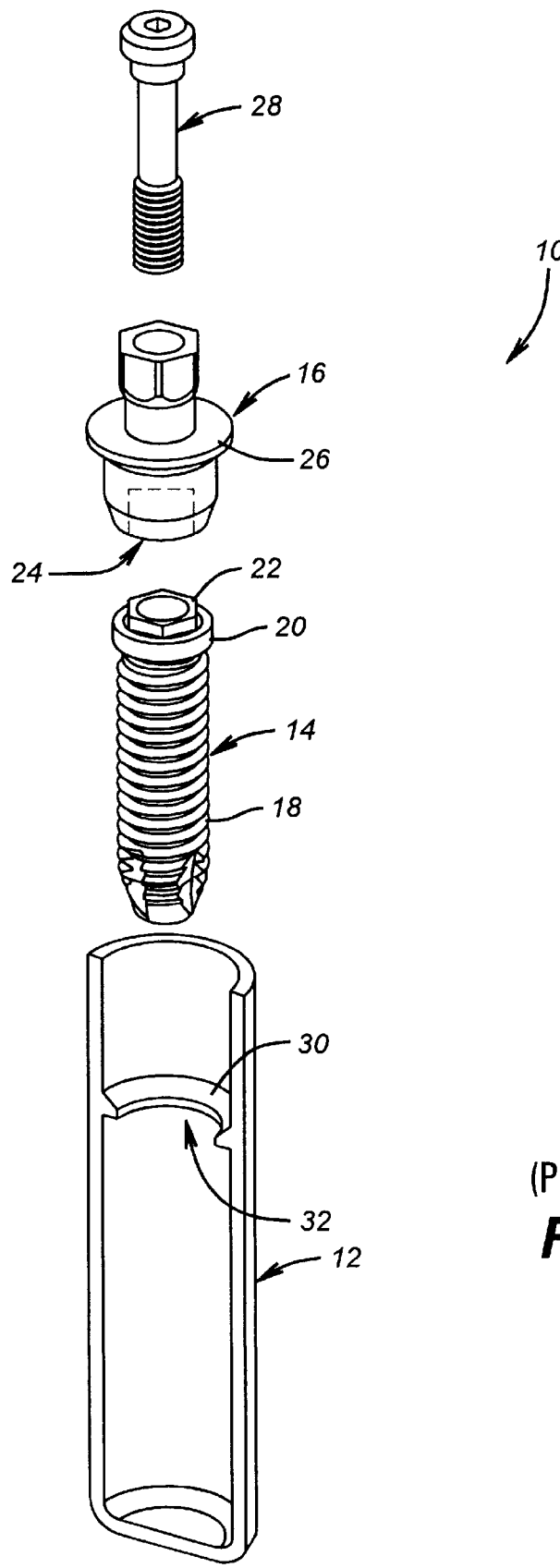
FIG. 1 is an exploded view of a prior dental delivery system.
Figure 2:
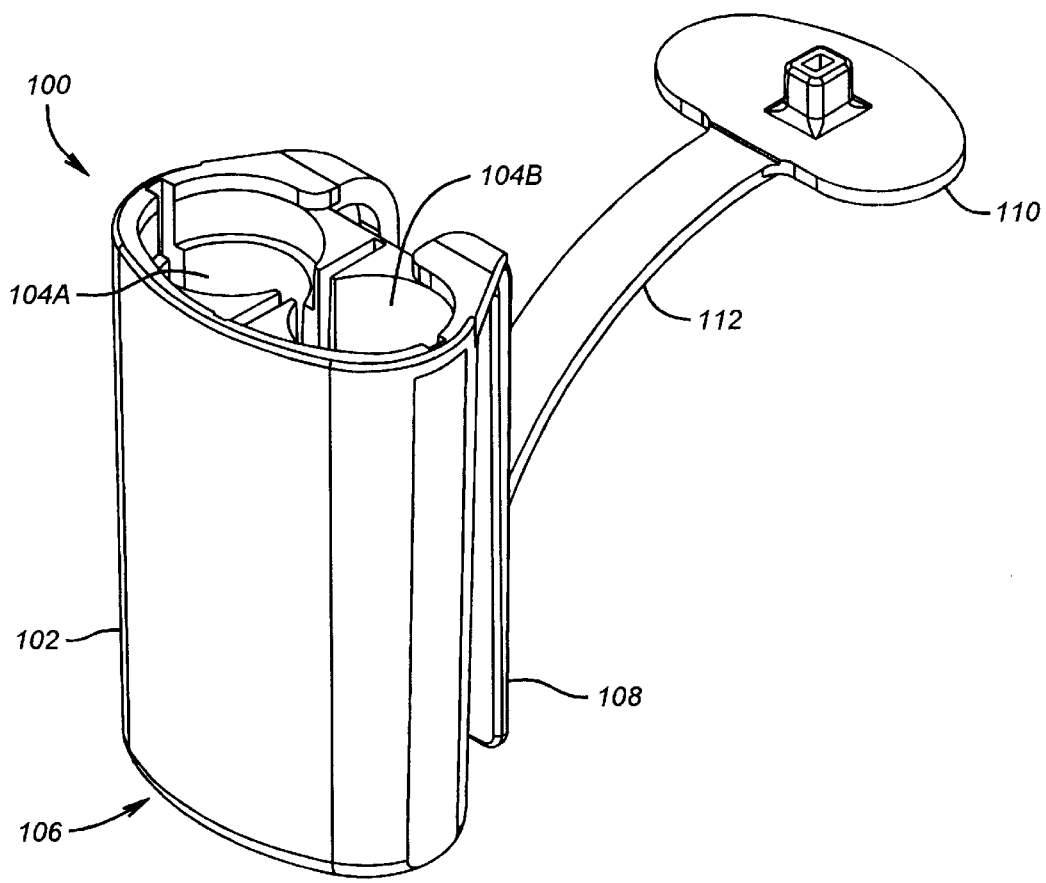
FIG. 2 is a perspective view of a vial for the dental delivery system of the present invention.

FIG. 2 illustrates a vial 100 of the dental implant delivery system. The vial includes a body 102 having two adjacent cavities 104A and 104B, respectively. Each cavity has a generally elongated cylindrical configuration that extends downwardly toward a closed base portion 106 of body 102. The vial also includes a clip 108 and a lid 110. The clip connects to a top portion of the body and is used to attach and secure the vial. A flexible arm 112 connects the lid to the body. It will be appreciated that the vial shown in FIG. 2 is exemplary, and other vial designs and configurations known to those skilled in the art also would be applicable with the present invention.

Figure 3:
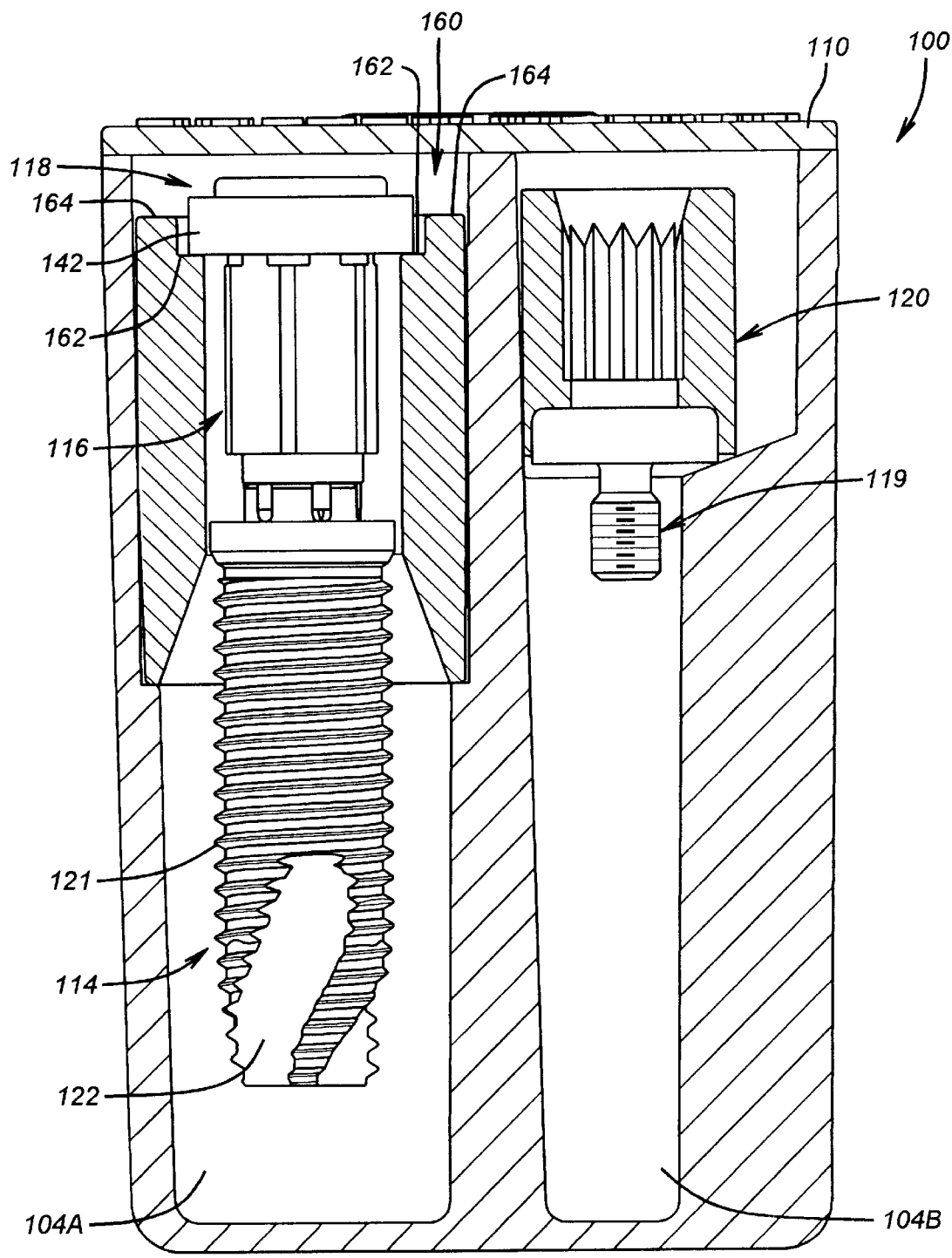
FIG. 3 is a cross sectional view of the vial of FIG. 2 having an implant, driver mount, and healing screw.
Figure 4:
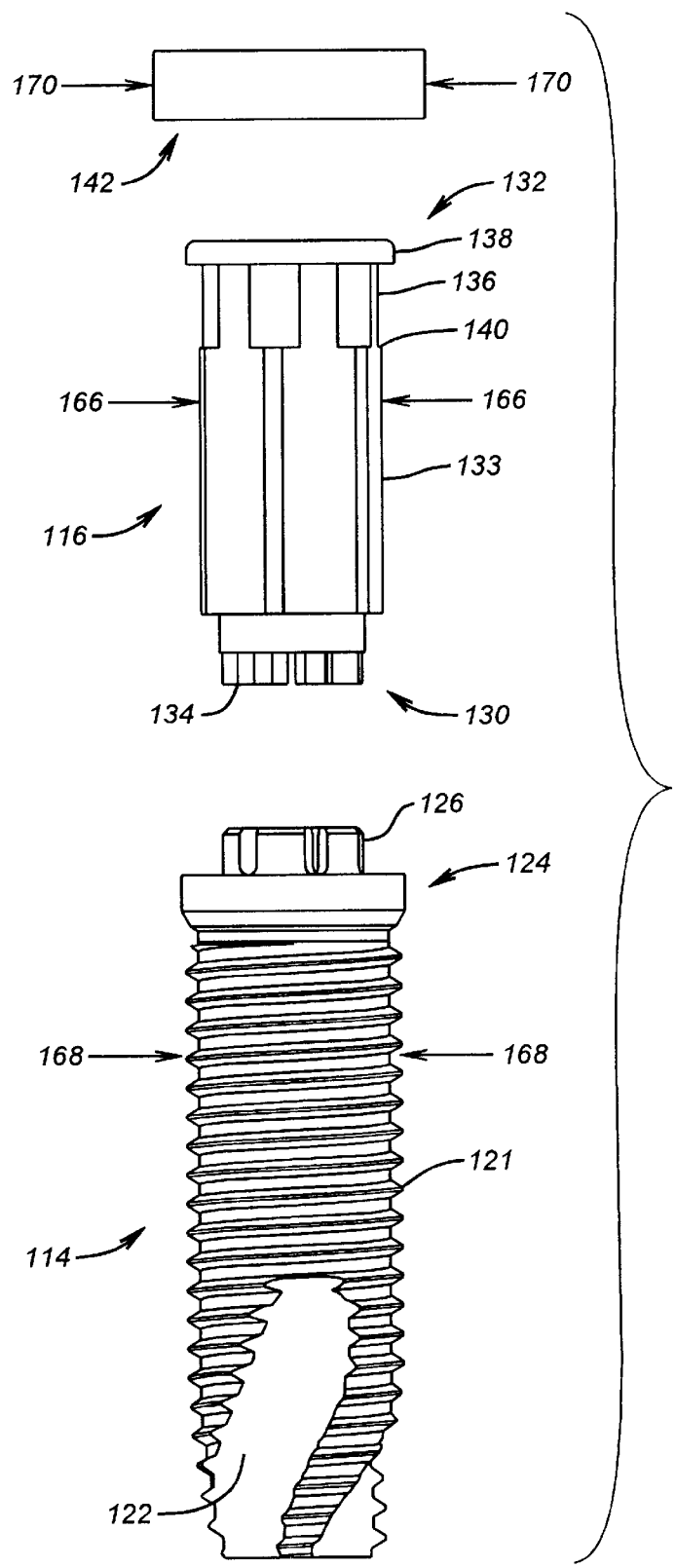
FIG. 4 is an exploded view of the implant, driver mount, and removable ring.

FIG. 3 shows a cross section of the implant delivery system that includes vial 100 housing in cavity 104A an implant 114, driver mount 116, and retaining screw 118. A healing screw 119 and removable mount 120 are located in cavity 104B. Turning also to FIG. 4, the implant and driver mount are shown in more detail.

Implant 114 may be any one of various implants known to those skilled in the art. For illustration purposes, implant 114 has outer threads 121, a cutting region 122 for self-tapping, and a coronal portion 124 having a plurality of splines 126 extending upwardly. This implant may be, for example, a TWIST implant manufactured by Sulzer Calcitek Inc. of Carlsbad, Calif.

Driver mount 116 has a generally elongated cylindrical configuration having two ends 130 and 132, respectively. Portions of the external surface 133 of the driver mount may be non-cylindrical, such as hexagonal. End 130 is configured to abut against the coronal end of the implant. End 130 includes a plurality of splines 134 that project downwardly to engage corresponding splines 126 of the implant. The engagement between these splines provides an anti-rotational connection between the driver mount and implant. This anti-rotational connection may be established with other configurations known to those skilled in the art, such as a mating hexagonal projection and recess.

Figure 5:
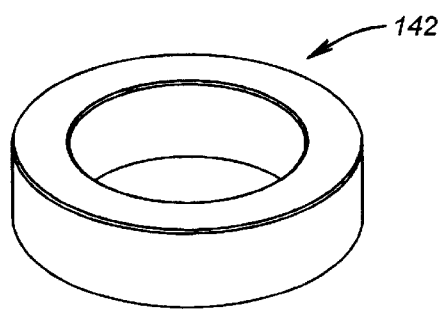
FIG. 5 is a first embodiment of the ring.

The other end 132 of the driver mount includes a channel 136 that circumferentially extends around the body. This channel is formed between a lip 138 located at the top of end 132 and shoulder 140. Channel 136 provides a space for a removable flange or ring 142. FIG. 5 illustrates one embodiment of ring 142 in more detail.

One important advantage of the present invention is that ring 142 is removable from the driver mount. Ring 142 is secured within channel 136 between lip 138 and shoulder 140. The ring though may be removed from this position around the driver mount. The ring, for example, may be pulled over lip 138 or shoulder 140 and removed from the channel.

Figure 6:
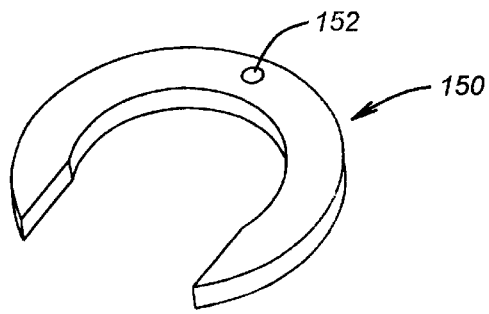
FIG. 6 is a second embodiment of the ring.

FIG. 6 illustrates another embodiment for the ring. Here, the ring is shaped like a thin C-clip 150. This clip fits around end 132 of the driver mount. The clip may connect, for example, with a snap-fit or frictional-fit. A small hole 152 is provided to aid in removing the clip from the driver mount. A tip of a dental instrument, such as an explorer, may be positioned in the hole and used to pull and remove the clip from the driver mount.

Use of the implant delivery system is now discussed in more detail with reference to FIGS. 3 and 4. During storage and transportation of the implant delivery system, the implant 114 and driver mount 116 remain suspended in a sterile and protected environment in vial 100. Cavity 104A includes an opening 160 forming a shoulder or ledge 162 within the cavity. The diameter through opening 160 and shoulder 162 is sufficiently large to enable the implant to pass freely into the cavity. Ring 142, affixed to the driver mount, is too large to pass through the opening. As such, the ring abuts against and rests on shoulder 162. The implant and driver mount are thus suspended within cavity 104A.

In FIG. 3, shoulder 162 exists slightly below opening 160. This shoulder, however, may exist at various positions in cavity 104A. The shoulder, for example, may be formed on top of opening 160 such that ring 142 rests on surface 164.

During a dental implantation procedure, lid 110 is removed from the top of vial 100 to expose the implant and driver mount. A driving tool, such as a motorized driver or ratchet wrench, and an adapter are then affixed to end 132 and the implant and driver mount are removed from the vial. The distal end of the implant is then positioned into the osteotomy site. The driving tool then imparts a driving force to the driver mount that, in turn, imparts this same force to the implant. Once the implant is fully seated and positioned, the driving tool is removed from end 132. The retaining screw 118 is then loosened, and the driver mount is removed from the implant. The implant remains in the bone, and the delivery cap 120 and healing screw 119 are then removed from cavity 104B using the noted driving tool. The cap is then placed over the coronal end of the implant until screw 119 fits within the implant. Thereafter, the cap 120 is disengaged from the screw, and the screw is left to cover the implant. Conventional procedures are then used to finish the surgical procedure and thereafter connect a prosthesis to the implant.

In some instances, the spacing available to receive the implant may be quite small. For example, the space between two adjacent teeth may be narrow. In this situation, the implant may be narrow enough to fit within this space, but the flange or ring on the driver mount may be too wide. If the flange or ring cannot safely fit within the available space, then the implant cannot be fully seated within the bone. The present invention solves this potential problem because the ring is removable from the driver mount. In such a situation, the ring would be removed from the driver mount enabling the implant to be fully and correctly positioned. Thus, a separate and narrower driver mount is not required.

Still looking to FIG. 4, the driver mount preferably has a diameter 166 equal to or less than the diameter 168 of the implant. The size of the driver mount thus does not obstruct or otherwise prohibit the placement of the implant in narrow dental spaces. The diameter 170 of the ring, however, is larger than diameter 166 of the driver mount and diameter 168 of the implant. As shown in FIG. 3, this difference in diameters enables the implant and part of the driver mount to pass through opening 160; the ring though is too large and rests on shoulders 162 to support the implant and driver mount.

The flange may be made to have any one of numerous configurations that may or may not resemble the embodiments of FIGS. 5 and 6. The term flange is defined broadly to describe a supporting feature that suspends the implant and driver mount in the vial. The flange, for example, may be formed as removable set screw or pin that protrudes through the end or side of the driver mount or formed as a protrusion, such as a ring or bead, that adhesively bonds to the end of the driver mount. The flange also may be formed as a shoulder, an elastomeric band, an O-ring, a C-clip, a toroid, U-shaped, star shaped, a cylindrical, or the like. Further, various materials may be used to fabricate the flange. The flange may be made from a polymer, steel, titanium, or other material suitable for use in restorative dentistry. Examples of such material include silicone, santoprene, delrin, polycarbonate, or PETG.

Since certain changes may be made in the above-described apparatus and method without departing from the scope of the invention herein involved, all matter contained in the description or shown in the accompanying drawings shall be interpreted as illustrative and not in a limiting sense.

The invention claimed is:

1. A dental implant delivery system, comprising:
    a vial having an opening leading to an internal cavity;
    a dental implant disposed within said cavity;
    a driver mount having a first end connected to said implant and a second end with a recess; and
    a separate flange disposed on said second end in said recess of said driver mount, said flange being removable from said driver mount and suspending said driver mount and said implant in said cavity.

2. The dental implant delivery system of claim 1 in which: said flange has a diameter too large to pass completely through said cavity;
    said driver mount has a diameter substantially equal to or less than a diameter of said implant; and
    said flange has a diameter greater than the diameters of both said implant and said driver mount.

3. The dental implant delivery system of claim 1 in which said flange is made of an elastic material.

4. The dental implant delivery system of claim 1 in which said flange is shaped as one of the following: an O-ring, a C-clip, a U-clip, a toroid, or a ring.

5. The dental implant delivery system of claim 1 in which said flange is shaped as a C-clip having a hole for receiving a dental tool.

6. The dental implant delivery system of claim 1 in which said cavity further comprises a ledge having a diameter smaller than a diameter of said flange and larger than a maximum diameter of both said implant and said driver mount.

7. A dental driver mount attachable to a dental implant having a coronal end with a first engaging feature, said driver mount comprising:
    a core body having first end with a second engaging feature that engages said first engaging feature to provide anti-rotation with said implant, and a second end oppositely disposed from said first end and having a recess; and
    a flange disposed within and removable from said recess of said core body.

8. The dental driver mount of claim 7 in which said recess is formed between a lip at a top of said first end and a shoulder disposed a distance from said lip.

9. The dental driver mount of claim 7 in which said flange is made from one of the following: a polymer, titanium, steel, a biocompatible material, or a metallic alloy.

10. The dental driver mount of claim 7 in which said flange is shaped as a C-clip, a U-clip, a toroid, a ring, a star, or a cylinder.

11. The dental driver mount of claim 7 in which said flange is a removable screw positioned through an end of said driver mount, a removable pin positioned through said end of said driver mount, or a ring adhesively attached to said end of said driver mount.

12. The dental driver mount of claim 7 in which:
    said driver mount has a diameter equal to or less than said implant; and
    said flange has a diameter greater than said diameters of said implant and said driver mount.

13. A method for implanting a dental implant into an opening between dentition in a jaw bone, comprising the steps of:
    providing a dental implant delivery system including a vial with a cavity and a ledge, a dental implant disposed within said cavity, a driver mount connected to said implant, and a removable flange connected to a recess around said said driver mount and positioned on said ledge to suspend said implant and driver mount within said cavity;
    connecting a driving tool to said driver mount;
    removing said implant, driver mount, and flange from said vial;
    removing said flange from said driver mount;
    positioning one end of said implant between said opening between said dentition in said jaw bone;
    driving said implant into said jaw bone;
    removing said driving tool from said driver mount; and
    removing said driver mount from said implant.

14. The method of claim 13 further comprising the step of cutting said flange to remove said flange from said driver mount.

15. The method of claim 13 further comprising the step of moving said flange off the end of said driver mount to remove said flange from said driver mount.

16. The method of claim 13 further comprising the steps of:
    providing said vial with a healing cap;
    removing said healing cap from said vial with said driving tool;
    positioning said healing cap on said implant; and
    removing said driving tool from said healing cap.

17. The method of claim 13 further comprising the step of:
    providing said flange with a hole;
    positioning the tip of a dental tool inside said hole; and
    pulling said flange with said tool to remove said flange from said driver mount.

* * * * *

UNITED STATES PATENT AND TRADEMARK OFFICE
CERTIFICATE OF CORRECTION

PATENT NO. : 6,086,371
DATED : 07/11/2000
INVENTOR(S): Bassett, et al.

It is certified that error appears in the above-identified patent and that said Letters Patent are hereby corrected as shown below:   On the title page: Item [73]
Assignee: delete "Sulzer Orthopedics Inc., Austin, Tex." and insert --Sulzer Calcitek Inc., Carlsbad, Calif.--

Signed and Sealed this

Twenty-fourth Day of April, 2001

Attest:

NICHOLAS P. GODICI

*Attesting Officer*                    *Acting Director of the United States Patent and Trademark Office*